(12) United States Patent
Prenzel et al.

(10) Patent No.: US 8,796,389 B2
(45) Date of Patent: Aug. 5, 2014

(54) METHOD FOR REVERSIBLE COVALENT CROSSLINKING OF ADHESIVES

(75) Inventors: Alexander Prenzel, Hamburg (DE); Sarah Bamberg, Hamburg (DE)

(73) Assignee: TESA SE, Hamburg (DE)

( * ) Notice: Subject to any disclaimer, the term of this patent is extended or adjusted under 35 U.S.C. 154(b) by 224 days.

(21) Appl. No.: 13/524,566

(22) Filed: Jun. 15, 2012

(65) Prior Publication Data

US 2012/0329956 A1    Dec. 27, 2012

(30) Foreign Application Priority Data

Jun. 21, 2011  (DE) .......................... 10 2011 077 927

(51) Int. Cl.
| | |
|---|---|
| C08F 8/40 | (2006.01) |
| C09J 133/02 | (2006.01) |
| C07F 9/6571 | (2006.01) |
| C08F 16/02 | (2006.01) |
| C08F 20/06 | (2006.01) |

(52) U.S. Cl.
CPC ......... *C09J 133/02* (2013.01); *C07F 9/657172* (2013.01); *C08F 16/02* (2013.01); *C08F 20/06* (2013.01); *C08F 2810/20* (2013.01); *C08F 8/40* (2013.01)
USPC ................. 525/340; 558/79; 558/78; 558/77; 558/76; 562/878

(58) Field of Classification Search
None
See application file for complete search history.

(56) References Cited

U.S. PATENT DOCUMENTS

| | | | | |
|---|---|---|---|---|
| 3,395,113 A | * | 7/1968 | Irani et al. ..................... | 524/124 |
| 4,507,416 A | * | 3/1985 | Chasar .......................... | 521/101 |
| 5,587,243 A | | 12/1996 | von Gentzkow et al. | |
| 5,756,638 A | * | 5/1998 | von Gentzkow et al. ..... | 528/108 |
| 5,789,487 A | | 8/1998 | Matyjaszewski et al. | |
| 5,854,364 A | | 12/1998 | Senninger et al. | |
| 5,945,491 A | | 8/1999 | Matyjaszewski et al. | |
| 6,479,608 B1 | | 11/2002 | Nesvadba et al. | |
| 6,933,361 B2 | | 8/2005 | Wudl et al. | |
| 2001/0031805 A1 | * | 10/2001 | Buhler ........................... | 524/99 |
| 2004/0014933 A1 | | 1/2004 | Wudl et al. | |
| 2008/0292848 A1 | | 11/2008 | Xie et al. | |
| 2009/0017004 A1 | * | 1/2009 | Zhao .......................... | 424/94.6 |
| 2011/0294948 A1 | * | 12/2011 | Urakawa et al. .............. | 524/558 |

FOREIGN PATENT DOCUMENTS

| | | |
|---|---|---|
| DE | 4308185 A1 | 9/1994 |
| DE | 19949352 A1 | 4/2000 |
| EP | 0658610 A1 | 6/1995 |
| JP | 1279921 | 11/1989 |
| WO | 9801478 A1 | 1/1998 |
| WO | 9931144 A1 | 6/1999 |
| WO | 2004081132 A1 | 9/2004 |
| WO | 2010092936 A1 | 8/2010 |

OTHER PUBLICATIONS

EP Search Report for EP 12171138 dated Oct. 23, 2012.
English language abstract for JP 1279921 which published Nov. 10, 1989.
English language abstract of EP0658610 published Jun. 21, 1995.
English language abstract of JP 01279921 published Nov. 10, 1989.
"Influence of Diluent and of Copolymer Composition on the Glass Temperature of a Polymer System", T.G. Fox, Rohm & Haas Company, published 1956.
"Macrommolecules", vol. 33, pp. 243-245, published 2000.
German Search Report for application DE 10 2011 077 927.2 dated Feb. 16, 2012.

\* cited by examiner

*Primary Examiner* — Robert C Boyle
(74) *Attorney, Agent, or Firm* — Norris McLaughlin & Marcus PA

(57) ABSTRACT

The present invention relates to a method for thermal crosslinking of adhesives and also to products produced with these adhesives. An object of the invention is to provide a method for thermal crosslinking of adhesives where the crosslinking is covalent and (initiated by a chemical or physical stimulus) reversible. As and when required, the crosslinking method can also be configured to result in a covalent, irreversible network.

12 Claims, No Drawings

METHOD FOR REVERSIBLE COVALENT CROSSLINKING OF ADHESIVES

This application claims priority to the German application DE 10 2011 077 927.2 filed Jun. 21, 2011.

The present invention relates to a method for thermal crosslinking of adhesives and also the products produced with these adhesives.

For a long time it has been known that for adhesives, more particularly for acrylate adhesives, crosslinking is necessary in order to generate outstanding adhesive properties. With rubbers as well, crosslinking produces an improvement in the adhesive properties.

In order to ensure sufficient stability of the adhesives towards high temperatures, solvents and other influences, preference is mostly given to methods, such as chemical/thermal crosslinking methods, for example, and also methods involving UV radiation or electron beams, that lead to the formation of a covalent crosslinking.

The adhesives produced by the aforementioned methods are usually irreversibly crosslinked, thereby restricting the use of adhesive tapes thus produced for specific applications, such as, for example, redetachability of the adhesive (either as an inherent quality or initiated by an external stimulus). The significance of the latter aspect in particular is growing markedly, in the light of increasing recycling circuits, especially for electronic and electrical products. On account of the increasing scarcity of raw materials, raw material prices have seen sharp increases, and consequently the disassembly and reutilisation of the electronic and electrical components have in turn become economic. For this purpose, the components, which because of the trend to miniaturisation in the electronics industry are more and more often bonded adhesively, must be able to be disassembled without damage to the components and without leaving excessive residues of the adhesive.

Appropriate first of all for such applications are reversible networks, which usually are based on physical interactions or can be generated by the use of coordinative cross linkers. WO 2004 081 132 A1, for example, describes reversible crosslinking with oil-soluble metal salts, but from the examples given it is readily apparent that this crosslinking mechanism is not suitable for producing thermally stable adhesives. Other examples of redetachable adhesive tapes based on a physical mechanism are given in US 2008 0 292 848 A1. In that case shape memory materials, i.e. materials which take on their original shape after a mechanical deformation, are used, but this increases the complexity of the product's construction, since the products must have a plurality of layers in order for such effects to be exploited.

Reactions such as Diels-Alder reactions are extremely suitable for generating thermally reversible, covalent networks. U.S. Pat. No. 6,933,361 B2 describes the preparation of polymers by means of polyfunctional furans and maleimides, which can be used as two-component systems for structural adhesive bonds. The selection of monomers for producing pressure-sensitive adhesive polymers is fairly limited, and their convertibility is difficult to implement, owing to the high reactivity or to side-reactions, using conventional polymerization processes (S. D. Bergman, F. Wudl, *J. Mater. Chem.* 2008, 18, 41-62).

Radiation-chemical crosslinking mechanisms are generally not suited to the production of reversible networks, since both UV crosslinking and electron-beam crosslinking are accompanied by formation of C—C bonds which cannot be broken thereafter.

EP 0 658 610 A1 describes a pressure-sensitive adhesive tape which is removable without residue. In this application text, the detachability of the pressure-sensitive adhesive is achieved through a reduction in the adhesion in combination with a generally weak attachment of the adhesive to the substrate. The use of such adhesive tapes is therefore confined to applications requiring only low bond strengths.

It is an object of the invention to provide a method for thermal crosslinking of adhesives where the crosslinking is covalent and (initiated by a chemical or physical stimulus) reversible. As and when required, the crosslinking method can also be configured to result in a covalent, irreversible network.

In the text below, the term "reversible" means that the covalent network can also be destroyed again by breaking the covalent bond, but that the network, after breaking of the covalent bond, cannot necessarily be reproduced, and hence "reversible" in most cases is synonymous with "reversible once".

Surprisingly it has been found that the use of cyclic phosphonic anhydrides in crosslinkable adhesive preparations—especially thermally crosslinkable adhesive preparations—in which at least some of the polymer components are functionalized with organic and/or inorganic, OH-group-containing acid units coupled to the polymer leads to outstanding crosslinked adhesives. The use of the cyclic phosphonic anhydrides activates the crosslinking reaction. In this way, reversibly crosslinked adhesives can be produced outstandingly. The cyclic phosphonic anhydride does not act as a crosslinking component, but instead activates the crosslinking between the acid groups, leading to a reversible crosslinking of the adhesive. It has emerged that the activator consumed in the crosslinking method does not, or not substantially, adversely affect the adhesive properties of the finished product.

Suitable organic and/or inorganic acid units containing OH groups are, for example, carboxylic acid groups, maleic acid groups, sulphonic acid groups and/or phosphonic acid groups; with particular preference, carboxylic acid groups are selected in accordance with the invention.

Crosslinking for the purposes of this specification means a reaction between polymer macromolecules that forms a three-dimensional network between these macromolecules. Thermal crosslinking means crosslinking initiated by thermal energy. Depending on the nature of the required activation, the thermal energy which is present at room temperature may already be sufficient for thermal crosslinking; in general, however, heating is undertaken, by means of active heating, in order to start the crosslinking, or the thermal energy is supplied in another way, for instance by mechanical influence (such as ultrasound) or by exothermic reaction processes in the reaction system. The influence of actinic (high-energy) radiation, such as ultra-violet rays, electron beams or radioactive rays, for instance, is not necessary. A crosslinking reaction initiated by actinic radiation can, however, be utilized in order to increase the efficiency of the thermal crosslinking. In the case of reversible crosslinking, the network formed can be broken down again (at least partly) by suitable measures, and so the macromolecules are present again in non-crosslinked form. In the case of irreversible crosslinking, the network cannot be parted again without destruction.

Adhesive preparations in accordance with the invention are mixtures and compositions which comprise at least crosslinkable (uncrosslinked and/or partly crosslinked, further crosslinkable) polymers, optionally further polymers and optionally adjuvants, the crosslinking of these preparations resulting in crosslinked polymer systems suitable as adhesives.

With great advantage the adhesive is a pressure-sensitive adhesive. A pressure-sensitive adhesive in this specification, as is customary in the general language, is a substance which, particularly at room temperature, is permanently tacky and also adhesive (referred to in the context of this specification as "pressure-sensitively adhesive" or else as "self-adhesive"). Characteristics of a pressure-sensitive adhesive are that it can be applied to a substrate by pressure and remains adhering thereon. Depending on the precise nature of the pressure-sensitive adhesive, the temperature and the atmospheric humidity, and also of the substrate, the effect of a short-term, minimal pressure, not going beyond a slight contact for a brief moment, may be sufficient to produce the adhesion effect; in other cases, a longer-term exposure to a high pressure may be necessary.

Pressure-sensitive adhesives have particular, characteristic viscoelastic properties, which result in the permanent tackiness and adhesiveness. Features of these adhesives include the fact that, when they are mechanically deformed, there are viscous flow processes and also the development of elastic resilience forces. The two processes have a certain relationship to one another in terms of their respective proportion, dependent not only on the precise composition, structure and degree of crosslinking of the pressure-sensitive adhesive in question, but also on the rate and duration of the deformation, and also on the temperature.

In addition to the acid functions which are attached to the polymer, it is also possible for one or more crosslinkers to have been added to the adhesive preparation for the purpose of increasing the efficiency of the reversible crosslinking. Suitable such crosslinkers are compounds functionalized by at least two acid functions, more particularly by carboxylic acid groups, maleic acid groups, sulphonic acid groups and/or phosphonic acid groups. The at least bifunctional crosslinkers may be monomeric, oligomeric or polymeric, with preferred additional crosslinkers being more particularly the shorter-chain crosslinkers, in other words which are monomeric or oligomeric.

Additionally, it has been found that the cyclic phosphonic anhydrides are likewise suitable as coupling reagents for irreversible crosslinking.

In one advantageous procedure in this case, the acid-functionalized adhesive preparation as described above further comprises at least one kind of functional groups suitable for entering into a reaction with acid groups present in the respective adhesive preparation, this reaction leading to covalent crosslinking. Functional groups suitable for this purpose include, for example, primary and secondary amines, primary, secondary and tertiary alcohols, phenols, 1,3-diketones and heteroaromatic compounds such as pyrazoles, for example. These additional functional groups may be attached to the carboxylic-, maleic-, sulphonic- and/or phosphonic-acid-containing polymers and/or to other polymers present in the adhesive composition.

Furthermore, in addition to the cyclic phosphonic anhydrides which function as coupling reagents, the adhesive preparation of the invention may be blended with crosslinkers which lead to irreversible crosslinking reactions. The crosslinkers preferably have at least two functional groups which are able to react with the acid groups of the polymer, these groups being advantageously of the type described above (in other words, in particular, primary and secondary amines, primary, secondary and tertiary alcohols, phenols, 1,3-diketones and heteroaromatic compounds such as pyrazoles, for example).

In an alternative procedure for the irreversible crosslinking, the polymers of the adhesive preparation are functionalized not with acid groups but instead wholly or partly with those functional groups as described above that are able to react with acid groups (in other words, in particular, primary and secondary amines, primary, secondary and tertiary alcohols, phenols, 1,3-diketones and heteroaromatic compounds such as pyrazoles, for example). In that case the adhesive preparation is also admixed with crosslinkers of the type described earlier on above for increasing the reversible crosslinking, in other words those—monomeric, oligomeric and/or polymeric—compounds which are functionalized by at least two acid functions—more particularly carboxylic acid groups, maleic acid groups, sulphonic acid groups and/or phosphonic acid groups. The activator used again is at least one cyclic phosphonic anhydride. In this case, by virtue of the reaction between the functional groups of the polymers in the adhesive preparation and the acid groups of the at least difunctional crosslinker, there is an irreversible crosslinking.

DETAILED DESCRIPTION OF THE INVENTION

In one preferred embodiment of the invention the cyclic phosphonic anhydride is a cyclic alkylphosphonic anhydride.

In a further-preferred inventive embodiment the cyclic alkylphosphonic anhydride is 2,4,6-substituted 1,3,5,2,4,6-trioxatriphosphinane 2,4,6-trioxide of the formula (I)

(I)

in which R independently at each occurrence stands for allyl, aryl or open-chain or branched C1 to C12 alkyl radicals, more particularly for C1-C8 alkyl radicals.

Particularly preferred are phosphonic anhydrides of the formula (I) in which R stands for a methyl, ethyl, n-propyl- (2,4,6-tripropyl-1,3,5,2,4,6-trioxatriphosphorinane 2,4,6-trioxide) (CAS No. 68957-94-8, tradename: Coupling Agent ° T3P from Archimica), isopropyl, n-butyl, 2-butyl, isobutyl, pentyl, hexyl, more particularly an ethyl, propyl and/or butyl radical.

The cyclic phosphonic anhydride may be added to the reaction medium either as a melt or as a liquid mixture in solution in a solvent. Suitable solvents here are those which do not result in side-reactions with the phosphonic anhydride, i.e. all aprotic organic solvents, such as, for example, ligroin, butane, pentane, hexane, heptane, octane, cyclobutane, cyclopentane, cyclohexane, cycloheptane, cyclooctane, dichloromethane, chloroform, carbon tetrachloride, 1,2-dichloroethane, 1,1,2,2-tetrachloroethane, methyl acetate, ethyl acetate, propyl acetate, butyl acetate, dimethylformamide, diethylformamide, dimethylacetamide, diethylacetamide, diethyl ether, diisopropyl ether, tert-butyl methyl ether, THF, dioxane, acetonitrile, acetone, butanone or mixtures of these, particular preference being given to dichloromethane, chloroform, ethyl acetate, propyl acetate, butyl acetate, dimethylformamide, diethylformamide, dimethylacetamide, diethylacetamide, diisopropyl ether, tert-butyl methyl ether, THF, dioxane, acetonitrile, acetone or mixtures of these, and very particular preference being given to THF, ethyl acetate, butyl acetate, acetone and butanone.

At least one of the components of the adhesive preparation is responsible for the crosslinked adhesive preparation, in other words the completed adhesive, having adhesive, more particularly pressure-sensitively adhesive properties. This component may be the one containing the acid groups, and/or the one which contains the optionally further functional groups. The respective groups may be provided instead of or in addition to one and/or two or more other components of the adhesive preparation.

The basis of the adhesives—more particularly pressure-sensitive adhesives—and also the (pressure-sensitive) adhesive tapes consisting of the aforementioned (pressure-sensitive) adhesives which are produced by means of the method of the invention encompasses all of the polymers and/or mixtures of polymers that are known to the skilled person and are suitable for producing adhesives and pressure-sensitive adhesives, respectively, provided that the polymers or at least one of the polymers in the polymer mixture have or has a functionality which can be activated by the cyclic phosphonic anhydride, in the manner set out above.

In one preferred variant, thermally crosslinkable, reversible, poly(meth)acrylate-based pressure-sensitive adhesives are used. The adhesive advantageously comprises a polymer consisting of
(a1) 70% to 100% by weight of acrylic esters and/or methacrylic esters and/or the corresponding free acids, with the formula (II)

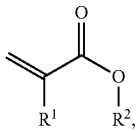

(II)

where $R^1$ represents H and/or $CH_3$ and $R^2$ represents H and/or alkyl chains having 1 to 30 C atoms;
(a2) 0% to 30% by weight of olefinically unsaturated monomers with functional groups; and
(a3) optionally further acrylates and/or methacrylates and/or olefinically unsaturated monomers (0% to 5% by weight) which are copolymerisable with component (a) and have a functional group which leads by means of the coupling reagent to a covalent, irreversible crosslinking.
The weight figures are based on the polymer.

For the monomers (a1) it is preferred to use acrylic monomers, comprising acrylic and methacrylic esters with alkyl groups, consisting of 1 to 14 C atoms. Specific examples, without wishing to be restricted by this recitation, are methyl acrylate, methyl methacrylate, ethyl acrylate, ethyl methacrylate, propyl acrylate, propyl methacrylate, n-butyl acrylate, n-butyl methacrylate, n-pentyl acrylate, n-hexyl acrylate, n-hexyl methacrylate, n-heptyl acrylate, n-octyl acrylate, n-nonyl acrylate, lauryl acrylate, stearyl acrylate, stearyl methacrylate, behenyl acrylate, and their branched isomers, such as 2-ethylhexyl acrylate, for example. Other classes of compound to be used, which can likewise be added in small amounts under (a1), are cyclohexyl methacrylates, isobornyl acrylate and isobornyl methacrylates.

For (a2) it is preferred to use monomers such as, for example, maleic anhydride, itaconic anhydride, glycidyl methacrylate, benzyl acrylate, benzyl methacrylate, phenyl acrylate, phenyl methacrylate, tert-butylphenyl acrylate, tert-butylphenyl methacrylate, phenoxyethyl acrylate, phenoxyethyl methacrylate, 2-butoxyethyl methacrylate, 2-butoxyethyl acrylate, dimethylaminoethyl methacrylate, dimethylaminoethyl acrylate, diethylaminoethyl methacrylate, diethylaminoethyl acrylate and tetrahydrofurfuryl acrylate, this recitation not being conclusive.

Also preferred for component (a2) is the use of aromatic vinyl compounds where the aromatic nuclei consist preferably of C4 to C18 building blocks and may also contain heteroatoms. Particularly preferred examples are styrene, 4-vinylpyridine, N-vinylphthalimide, methylstyrene and 3,4-dimethoxystyrene, this recitation not being conclusive.

Particularly preferred examples for component (a3) are hydroxyethyl acrylate, 3-hydroxypropyl acrylate, hydroxyethyl methacrylate, 3-hydroxypropyl methacrylate, 4-hydroxybutyl acrylate, 4-hydroxybutyl methacrylate, allyl alcohol, itaconic acid, acrylamide and cyanoethyl methacrylate, cyanoethyl acrylate, 6-hydroxyhexyl methacrylate, N-tert-butylacrylamide, N-methylolmethacrylamide, N-(butoxymethyl)methacrylamide, N-methylolacrylamide, N-(ethoxymethyl)acrylamide, N-isopropylacrylamide, vinylacetic acid, β-acryloyloxypropionic acid, trichloroacrylic acid, fumaric acid, crotonic acid, aconitic acid, dimethylacrylic acid, 4-vinylbenzoic acid, this recitation not being conclusive.

For the polymerization the monomers are selected such that the resultant polymers can be used as thermally crosslinkable pressure-sensitive adhesives, more particularly such that the resulting polymers possess pressure-sensitive adhesive properties in accordance with the "Handbook of Pressure Sensitive Adhesive Technology" by Donatas Satas (van Nostrand, N.Y. 1989).

The nature of the comonomers is selected such that the glass transition temperature $T_g$, of the polymers is below the utility temperature, preferably $T_{g,A} \leq 15°$ C. In order to achieve this, additionally, the quantitative composition of the monomer mixture is advantageously selected such that the Fox equation (E1) (cf. T. G. Fox, Bull. Am. Phys. Soc. 1956, 1, 123) produces the desired $T_{g,A}$ value for the polymer.

$$\frac{1}{T_g} = \sum_n \frac{w_n}{T_{g,n}} \tag{E1}$$

In this equation, n represents the serial number of the monomers used, $W_n$ the mass fraction of the respective monomer n (% by weight) and $T_{g,n}$ the respective glass transition temperature of the homopolymer of the respective monomer n, in K.

For preparing the polyacrylate PSAs (pressure-sensitive adhesives) it is advantageous to carry out conventional radical polymerizations or controlled radical polymerizations. For the polymerizations which proceed by a radical mechanism it is preferred to use initiator systems which additionally contain further radical initiators for the polymerization, more particularly thermally decomposing radical-forming azo or peroxo initiators. Suitability is possessed in principle, however, by all customary initiators that are familiar to the skilled person for acrylates and/or methacrylates. The production of C-centred radicals is described in Houben-Weyl, Methoden der Organischen Chemie, Vol. E 19a, pp 60-147. These methods are preferentially employed analogously.

Examples of radical sources are peroxides, hydroperoxides and azo compounds. As a number of non-exclusive examples of typical radical initiators, mention may be made here of potassium peroxodisulfate, dibenzoyl peroxide, cumene hydroperoxide, cyclohexanone peroxide, di-tert-butyl peroxide, azobisisobutyronitrile, cyclohexylsulphonyl acetyl peroxide, diisopropyl percarbonate, tert-butyl peroctoate and benzpinacol. A particularly preferred radical initiator used is 1,1'-azobis(cyclohexanecarbonitrile) (Vazo 88™ from DuPont).

The average molecular weights Mn of the PSAs formed in the radical polymerization are very preferably selected such that they are in a range from 20 000 to 2 000 000 g/mol; it is preferred to prepare PSAs having average molecular weights Mw of 200 000 to 1 200 000 g/mol. The average molecular weight is determined by gel permeation chromatography (GPC).

The polymerization may be carried out in bulk, in the presence of one or more organic solvents, in the presence of water or in mixtures of organic solvents and water. The aim here is to minimize the amount of solvent used. Suitable organic solvents are pure alkanes (e.g. hexane, heptane, octane, isooctane), aromatic hydrocarbons (e.g. benzene, toluene, xylene), esters (e.g. ethyl acetate, propyl, butyl or hexyl acetate), halogenated hydrocarbons (e.g. chlorobenzene), alkanols (e.g. methanol, ethanol, ethylene glycol, ethylene glycol monomethyl ether), ketones (e.g. acetone, butanone) and ethers (e.g. diethyl ether, dibutyl ether) or mixtures thereof. The aqueous polymerization reactions may be admixed with a water-miscible or hydrophilic co-solvent, in order to ensure that the reaction mixture is in the form of a homogeneous phase during monomer conversion. Co-solvents which can be used advantageously for the present invention are selected from the following group, consisting of aliphatic alcohols, glycols, ethers, glycol ethers, pyrrolidines, N-alkylpyrrolidinones, N-alkylpyrrolidones, polyethylene glycols, polypropylene glycols, amides, carboxylic acids and salts thereof, esters, organic sulphides, sulphoxides, sulphones, alcohol derivatives, hydroxylether derivatives, amino alcohols, ketones and the like, and also derivatives and mixtures thereof.

The polymerization time—depending on conversion and temperature—is between 4 and 72 hours. The higher the reaction temperature that can be selected, in other words the higher the thermal stability of the reaction mixture, the lower the reaction time that can be selected.

For initiating the polymerization, the introduction of heat is essential for the thermally decomposing initiators. For the thermally decomposing initiators the polymerization can be initiated by heating to 50 to 160° C., depending on initiator type.

For radical stabilization, use is made, in an advantageous procedure, of nitroxides, such as, for example, 2,2,5,5-tetramethyl-1-pyrrolidinyloxyl (PROXYL), 2,2,6,6-tetramethyl-1-piperidinyloxyl (TEMPO), derivatives of PROXYL or of TEMPO, and other nitroxides familiar to the skilled person.

A series of further polymerization methods whereby the adhesives can be prepared in an alternative procedure can be selected from the prior art: WO 96/24620 A1 describes a polymerization process in which highly specific radical compounds such as, for example, phosphorus-containing nitroxides based on imidazolidine are used. WO 98/44008 A1 discloses specific nitroxyls based on morpholines, piperazinones and piperazinediones. DE 199 49 352 A1 describes heterocyclic alkoxyamines as regulators in controlled-growth radical polymerizations.

As a further controlled polymerization method it is possible in an advantageous way, for the synthesis of block copolymers, to use Atom Transfer Radical Polymerization (ATRP), the initiator used preferably comprising monofunctional or difunctional secondary or tertiary halides and, for abstracting the halide or halides, complexes of Cu, Ni, Fe, Pd, Pt, Ru, Os, Rh, Co, Ir, Ag or Au. The various possibilities of the ATRP are further described in the texts of U.S. Pat. No. 5,945,491 A, of U.S. Pat. No. 5,854,364 A and of U.S. Pat. No. 5,789,487 A.

A very preferred production procedure carried out is a variant of the RAFT polymerization (reversible addition-fragmentation chain transfer polymerization). The polymerization procedure is described comprehensively in the texts WO 98/01478 A1 and WO 99/31144 A1, for example. Suitable with particular advantage for the preparation are trithiocarbonates of the general structure R'''—S—C(S)—S—R''' (*Macromolecules* 2000, 33, 243-245).

In one very advantageous variant, for example, the trithiocarbonates (TTC1) and (TTC2) or the thio compounds (THI1) and (THI2) are used for the polymerization, where φ may be a phenyl ring, which may be unfunctionalised or functionalised by alkyl or aryl substituents, attached directly or via ester or ether bridges, or may be a cyano group or a saturated or unsaturated aliphatic radical. The phenyl ring φ may optionally carry one or more polymer blocks, examples being polybutadiene, polyisoprene, polychloroprene or poly(meth)acrylate, which may have a construction in accordance with the definition for P(A) or P(B), or may carry polystyrene, to name but a few. Functionalisations may be, for example, halogens, hydroxyl groups, epoxide groups, nitrogen-containing or sulphur-containing groups, without this recitation making any claim to completeness.

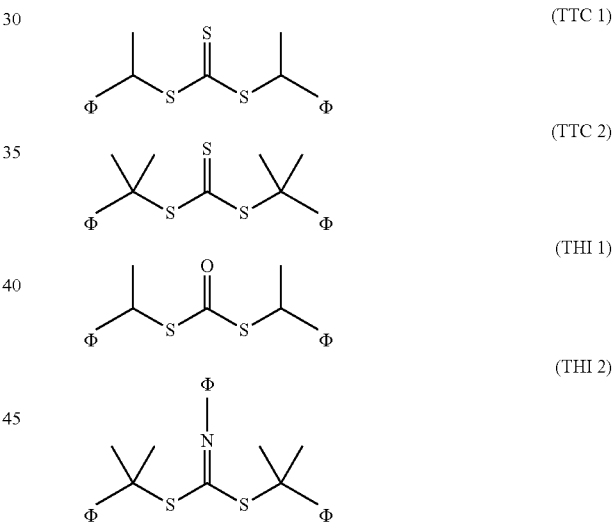

In conjunction with the aforementioned controlled-growth polymerizations proceeding by radical mechanism, preference is given to initiator systems which additionally contain further radical initiators for the polymerization, more particularly the thermally decomposing radical-forming azo or peroxo initiators already recited above. In principle, however, all customary initiators known for acrylates and/or methacrylates are suitable. Furthermore, it is also possible to use radical sources which release radicals only under UV irradiation.

In further, advantageous embodiments of the invention, other polymers, suitable and known to the skilled person for the production of PSAs, are used, exhibiting a functionality which through activation with a cyclic phosphonic anhydride leads to the formation of a reversible and/or irreversible crosslinking. By way of example, but without restriction, mention may be made of acid-modified or maleic anhydride-modified saturated and/or unsaturated synthetic rubbers and styrene block copolymers, partially hydrogenated polyvinyl acetate, partially hydrogenated EVA systems, polyurethanes, polyesters and silicones.

For advantageous further development it is possible for resins to be admixed to the adhesives, more particularly to the pressure-sensitive adhesives. Tackifying resins which can be used are the tackifier resins that are in principle already known and are described in the literature. Representatives include the pinene resins, indene resins and rosins, their disproportionated, hydrogenated, polymerized and esterified derivatives and salts, the aliphatic and aromatic hydrocarbon resins, terpene resins and terpene-phenolic resins, and also C5, C9 and other hydrocarbon resins. Any desired combinations of these and further resins may be used in order to adjust the properties of the resultant adhesive in accordance with requirements. Generally speaking, it is possible to use any resins that are compatible (soluble) with the corresponding adhesive; reference may be made more particularly to all aliphatic, aromatic and alkylaromatic hydrocarbon resins, hydrocarbon resins based on pure monomers, hydrogenated hydrocarbon resins, functional hydrocarbon resins and natural resins. Express reference may be made to the depiction of the state of knowledge in the "Handbook of Pressure Sensitive Adhesive Technology" by Donatas Satas (van Nostrand, 1989).

It is possible, furthermore, optionally to add plasticizers (plasticizing agents), fillers (e.g. fibres, carbon black, zinc oxide, titanium dioxide, chalk, solid or hollow glass beads, mitrobeads of other materials, silica, silicates), nucleators, expandants, compounding agents and/or ageing inhibitors, in the form, for example, of primary and secondary antioxidants or in the form of light stabilisers.

The aforementioned resins and/or additives, the belowmentioned (more particularly irreversible) crosslinkers, and also any further adjuvants are typically added to the adhesive preparation before and/or during the reversible crosslinking activated by the phosphonic anhydride, unless this is deleterious for the crosslinking method.

For the anchoring of the adhesives on a substrate, as for example on a backing for producing adhesive tape, it can be advantageous if the polymer is treated by corona or plasma prior to coating. Instruments from Plasmatreat, for example, are suitable for atmospheric plasma treatment.

Furthermore, for the procedure and for the anchoring of the layer with further possible layers, with a film based on polyester, polyamide, polymethacrylate, PVC, etc., or with a viscoelastic foamed or unfoamed backing based on polyacrylate or polyurethane, it may be of advantage if there is a chemical anchoring, by way of a primer, for example.

The internal strength (cohesion) of the adhesive is preferably increased by crosslinking. Particularly preferred are PSAs, more particularly polyacrylate-based PSAs, which are reversibly crosslinkable. In order then to ensure that the adhesive possesses a consistent profile of properties, the reversible covalent crosslinking is preferably selected such that the network is destroyed only by an external stimulus.

Surprisingly it has been found that adhesives (more particularly PSAs) which have been crosslinked by means of a cyclic phosphonic anhydride as coupling reagent become redetachable by treatment with acidic or basic aqueous solutions and also alkanol-based solvents, but that the crosslinking is stable with respect to all other influences and also with respect to water, increased atmospheric humidity and other organic solvents.

The adhesives (more particularly PSAs) may optionally be admixed, in addition to the cyclic phosphonic anhydrides, with compatible crosslinker substances, in order to raise the efficiency of the reversible crosslinking and/or to produce an irreversible crosslinking. Examples of corresponding crosslinker substances have already been described earlier on above.

In a further advantageous embodiment, for the formation of an irreversible network, it is possible, alternatively to the aforementioned crosslinkers or in addition to them, to select those crosslinkers which are not activated by the cyclic phosphonic anhydrides, such as, for example, metal chelates, polyfunctional isocyanates, polyfunctional epoxides, polyfunctional aziridines, polyfunctional oxazolines or polyfunctional carbodiimides. Polyfunctional acrylates as well can be used with advantage as crosslinkers for actinic irradiation.

A crosslinking method in which two different crosslinking reactions are performed, such as, more particularly, a thermal crosslinking and an actinic crosslinking, is also referred to as a "dual-cure" method. A dual-cure method of this kind is likewise considered inventive in the context of this specification. With particular advantage a thermal crosslinking is carried out which is activated with cyclic phosphonic anhydrides, and additionally a radiation-initiated crosslinking, more particularly as described in the context of this specification, which is initiated advantageously by ultraviolet radiation (UV rays) and/or by electron beams (EBC).

The adhesives of the invention described above, more particularly pressure-sensitive adhesives, are outstandingly suitable for the production of single-sided or double-sided adhesive tapes, where all of the carrier materials familiar to the skilled person can be used. Useful carrier materials include by way of example, but are not limited to, PET, PVC and PP films, paper, nonwovens, woven fabrics, and foams.

For transport, storage or diecutting, the adhesive tapes is preferably provided on at least one side with a liner, in other words, for example, with a silicone-coated film or silicone paper.

A further advantageous embodiment of the invention is the use of a carrier-free adhesive for the self-adhesive tape. A carrier-free adhesive is an adhesive which does not have a permanent carrier, such as a polymer film or a nonwoven. Instead, in a preferred embodiment, the self-adhesive material is applied solely to a liner, in other words to a material which serves only temporarily for the support and greater ease of application of the self-adhesive material. Following the application of the self-adhesive material to the substrate surface, the liner is then removed, and the liner, therefore, does not constitute a productive component.

In a further advantageous embodiment of the invention, the method for producing the adhesives can also be utilised in order to produce viscoelastic foamed or unfoamed layers which serve as carriers and are additionally laminated on at least one side with a pressure-sensitive adhesive.

The pressure-sensitive adhesives of the invention can be prepared from solution and also from the melt. For the latter case, suitable preparation procedures include both batch processes and continuous processes. Particularly preferred is continuous manufacture by means of an extruder with subsequent coating directly onto a liner with or without a layer of adhesive.

The present invention further provides for the use of an adhesive tape—more particularly a self-adhesive tape—with the reversibly and covalently crosslinked (pressure-sensitive) adhesive of the invention, more preferably a polyacrylate-based pressure-sensitive adhesive, for the bonding of electronic components, it being rational, on account of the ever more highly rising raw materials prices, for such components to be reused. The adhesive—more particularly a self-adhesive—is selected, more particularly in accordance with the requirements described above, in such a way that it can be removed without residue by an external stimulus, preferably by treatment with acidic or basic aqueous solutions or alkanol-based solvents, thus allowing the electronic component to be uninstalled without destruction, and reused. Furthermore, the adhesive ought to have a very high temperature resistance, in order to allow as great as possible a diversity of fields of use in electronic components. Provision is made more particularly for the adhesive to be temperature-resistant down to −5° C., preferably down to −15° C., more preferably down to −30° C. Moreover, the adhesive ought also to be temperature-resistant up to 70° C., preferably up to 80° C., more preferably up to 100° C.

In the text below, the invention is illustrated in more detail using the examples, without thereby limiting the invention.

Experimental Section

Unless anything alternative is indicated or becomes apparent in any particular case, the sample preparations and the measurements take place under standard conditions (25° C., 101325 Pa).

I. Static Glass Transition Temperature Tg.

The static glass transition temperature is determined by dynamic scanning calorimetry in accordance with DIN 53765. The figures for the glass transition temperature Tg refer to the glass transition temperature value Tg according to DIN 53765:1994-03, unless indicated otherwise in the specific instance.

II. Molecular Weights

The average molecular weights (weight average Mw and number average Mn) and the polydispersity D were determined by gel permeation chromatography (GPC). The eluent used was THF with 0.1% by volume of trifluoroacetic acid. Measurement took place at 25° C. The preliminary column used was PSS-SDV, 5 µm, 103 Å (10-7 m), ID 8.0 mm×50 mm, Separation was carried out using the columns PSS-SDV, 5 µm, 103 Å (10-7 m), 105 Å (10-5 m) and 106 Å (10-4 m) each of ID 8.0 mm×300 mm. The sample concentration was 4 g/l, the flow rate 1.0 ml per minute. Measurement was made against PMMA standards.

III. Solids Content:

The solids content is a measure of the fraction of unvaporisable constituents in a polymer solution. It is determined gravimetrically, by weighing the solution, then evaporating off the vaporizable fractions in a drying oven at 120° C. for 2 hours, and weighing the residue again.

IV. K Value (According to Fikentscher):

The K value is a measure of the average molecular size of high-polymer compounds. It is measured by preparing one percent strength (1 g/100 ml) toluenic polymer solutions and determining their kinematic viscosities by means of a VOGEL-OSSAG viscometer. Standardisation to the viscosity of the toluene gives the relative viscosity, from which the K value can be calculated by the method of Fikentscher (Polymer 8/1967, 381 ff.)

V. Quantitative Determination of the Shear Strength: Static Shear Test HP

A rectangular test specimen measuring 13 mm×20 mm of the double-sided adhesive tape under test is bonded between two steel plaques (50 mm×25 mm×2 mm; material as per DIN EN 10088-2, type 1, 4301, surface quality 2R, cold-rolled and bright-annealed, Ra=25-75 nm) in such a way that the bond area of the test specimen with both steel plaques is 260 mm² in each case; the steel plaques are oriented in parallel with an offset in the longitudinal direction, and so the test specimen is bonded centrally between them and the steel plaques protrude beyond the test specimen on different sides. The bonded assembly is then pressed for 1 minute with an applied pressure of 100 N/cm². After a specified time for the bond to take (unless otherwise indicated, 72 hours at room temperature), the test elements prepared in this way are suspended, by one steel plaque region protruding beyond the test specimen, on a shear test measurement area, in such a way that the longitudinal direction of the steel plaques points downwards, and the region of the other steel plaque that protrudes beyond the test specimen is loaded, at a specified temperature, with a selected weight (measurements at room temperature and with 20 N load, and at 70° C. and with 10 N load; see details in the respective table). Test conditions: standard conditions, 50% relative humidity.

An automatic clock then determines the time elapsing until failure of the test specimens, in minutes (the steel plaque under load drops off).

VI. Peel Strength (Bond Strength) BS

A strip of the (pressure-sensitive) adhesive tape under investigation is bonded in a defined width (standard: 20 mm) to a sanded steel plate (stainless steel 302 according to ASTM A 666; 50 mm×125 mm×1.1 mm; bright annealed surface; surface roughness Ra=50±25 nm average arithmetic deviation from the baseline) by being rolled on ten times with a 5 kg steel roller. Double-sided adhesive tapes are reinforced on the reverse with an unplasticised PVC film 36 µm thick. Identical samples are produced and are alternatively provided for immediate measurement, stored for 3 days and subjected to measurement, or stored for 14 days and subjected to measurement.

The prepared plate is clamped (fixed) into the testing apparatus, and the adhesive strip is peeled from the plate via its free end in a tensile testing machine at a peel angle of 90° and at a speed of 300 mm/min in the longitudinal direction of the adhesive tape. The force necessary for performing this operation is recorded. The results of the measurements are reported in N/cm (force standardised to the particular section of adhesive bond parted) and are averaged over three measurements. All of the measurements are carried out in a controlled-climate chamber at 23° C. and 50% relative humidity.

VII. Microshear Test

This test serves for the accelerated testing of the shear strength of adhesive tapes under temperature load.

Sample Preparation for Microshear Test:

An adhesive tape (length about 50 mm, width 10 mm) cut from the respective sample specimen is bonded to a steel test plate, cleaned with acetone, so that the steel plate protrudes beyond the adhesive tape to the right and left, and so that the adhesive tape protrudes beyond the test plate by 2 mm at the top edge. The bond area of the sample in terms of height·width=13 mm·10 mm. The bond site is subsequently rolled over six times with a 2 kg steel roller at a speed of 10 m/min. The adhesive tape is reinforced flush with a stable adhesive strip which serves as a support for the travel sensor. The sample is suspended vertically by means of the test plate.

Microshear Test:

The sample specimen under measurement is loaded at the bottom end with a 100 g weight. The test temperature is 40° C., the test time 30 minutes (15 minutes' loading and 15 minutes' unloading). The shear travel after the specified test duration at constant temperature is reported as the result, in µm, as both the maximum value ["max"; maximum shear travel as a result of 15-minute loading]; and the minimum value ["min"; shear travel ("residual deflection") 15 minutes after unloading; on unloading there is a backward movement as a result of relaxation]. Likewise reported is the elastic component in percent ("elast"; elastic component=(max−min)·100/max].

TABLE 1

Raw materials used:

| Chemical compound | Tradename | Manufacturer | CAS No. |
|---|---|---|---|
| Bis(4-tert-butylcyclohexyl) peroxydicarbonate | Perkadox ® 16 | Akzo Nobel | 15520-11-3 |
| 2,2'-Azobis(2-methylbutyronitrile) | Vazo ® 67 | DuPont | 13472-08-7 |
| 2,4,6-Tripropyl-1,3,5,2,4,6-trioxatriphosphorinane 2,4,6-trioxide | Coupling Agent ® T3P | Archimica | 68957-94-8 |
| Aluminium(III) acetylacetonate | | Sigma-Aldrich | 13963-57-0 |
| Low-viscosity aliphatic polyisocyanate resin based on hexamethylene diisocyanate | Desmodur ® N 3900 | Bayer Material Science | 28182-81-2 |
| Acrylic acid n-butyl ester | n-Butyl acrylate | Rohm & Haas | 141-32-2 |
| Acrylic acid | acrylic acid, pure | BASF | 79-10-7 |
| 2-Ethylhexyl acrylate | | Brenntag | 103-11-7 |
| 2-Hydroxyethyl methacrylate | Bisomer ™ HEMA | Cognis | 868-77-9 |

In the text below, for the coupling reagents and crosslinkers 2,4,6-tripropyl-1,3,5,2,4,6-trioxatriphosphorinane 2,4,6-trioxide and aluminium(III) acetylacetonate, the designations T3P and Al(acac)$_3$ are used.

Preparation of Base Polymer Ac1

A reactor conventional for radical polymerizations was charged with 30.0 kg of 2-ethylhexyl acrylate, 67.0 kg of butyl acrylate, 3.0 kg of acrylic acid and 66.7 kg of acetone/isopropanol (96:4). After nitrogen gas had been passed through the reactor for 45 minutes, with stirring, the reactor was heated to 58° C. and 50 g of Vazo 67, in solution in 500 g of acetone, were added. The external heating bath was then heated to 70° C. and the reaction was carried out constantly at this external temperature. After 1 hour a further 50 g of Vazo 67, in solution in 500 g of acetone, were added, and after 2 hours the batch was diluted with 10 kg of acetone/isopropanol mixture (96:4). After 5.5 hours, 150 g of bis(4-tert-butylcyclohexyl)peroxydicarbonate, in solution in 500 g of acetone, were added; after 6 hours 30 minutes, dilution took place again with 10 kg of acetone/isopropanol mixture (96:4). After 7 hours a further 150 g of bis(4-tert-butylcyclohexyl)peroxydicarbonate, in solution in 500 g of acetone, were added and the heating bath was set to a temperature of 60° C.

After a reaction time of 22 hours, the polymerization was discontinued and the batch was cooled to room temperature. The product had a solids content of 50.2% and was dried. The resulting polyacrylate had a K value of 75.2, a weight-average molecular weight of Mw=1 370 000 g/mol, a polydispersity of D (Mw/Mn)=17.13 and a static glass transition temperature of Tg=−38.0° C.

Preparation of Base Polymer Ac2:

A reactor conventional for radical polymerizations was charged with 30.0 kg of 2-ethylhexyl acrylate, 66.0 kg of butyl acrylate, 1.0 kg of 2-hydroxyethyl methacrylate, 3.0 kg of acrylic acid and 64.3 kg of acetone/isopropanol (95:5). After nitrogen gas had been passed through the reactor for 45 minutes, with stirring, the reactor was heated to 58° C. and 50 g of Vazo 67, in solution in 500 g of acetone, were added. The external heating bath was then heated to 75° C. and the reaction was carried out constantly at this external temperature. After 1 hour a further 50 g of Vazo 67, in solution in 500 g of acetone, were added, and after 4 hours the batch was diluted with 12.1 kg of acetone/isopropanol mixture (95:5).

After 5 hours and again after 7 hours, 150 g each time of bis(4-tert-butylcyclohexyl)peroxydicarbonate, in solution in 500 g of acetone in each case, were added for re-initiation. After a reaction time of 22 hours, the polymerization was discontinued and the batch was cooled to room temperature. The product had a solids content of 50.2% and was dried. The resulting polyacrylate had a K value of 72.9, a weight-average molecular weight of Mw=1 040 000 g/mol, a polydispersity of D (Mw/Mn)=8.7 and a static glass transition temperature of Tg=−59.0° C.

EXAMPLES

Preparation of Pressure-Sensitive Adhesive PSA1 to PSA6

TABLE 2

Adhesive-specific data

| Name | Base polymer | Coupling reagent/ crosslinker | Crosslinker fraction [% by weight] |
|---|---|---|---|
| PSA1 | Ac1 | — | — |
| PSA2 | Ac1 | T3P | 0.47 |
| PSA3 | Ac1 | Al(acac)$_3$ | 0.25 |
| PSA4 | Ac2 | T3P | 0.47 |
| PSA5 | Ac2 | Al(acac)$_3$ | 0.25 |
| PSA6 | Ac2 | Desmodur N 3900 | 0.2 |

0.47% by weight of T3P corresponds to 3.5 mol % based on the acrylic acid fraction of the polymer.

The base polymer in solution was blended in each case with a 3% strength solution of the coupling reagent or crosslinker in isopropanol, diluted with isopropanol to a solids content of 30%, and then coated from solution onto a siliconised release film (50 μm polyester). (Coating speed 2.5 m/min, drying tunnel 15 m, temperatures zone 1: 40° C., zone 2: 70° C., zone 3: 95° C., zone 4: 105° C.). The coatweight was 50 g/m$^2$ in each case.

TABLE 3

Adhesive performance results

| Pressure-sensitive adhesive | Bond strength to steel [N/cm] | Bond strength to PE [N/cm] | Holding power [min] |
|---|---|---|---|
| PSA1 | 7.5 | 3.02 | 0 |
| PSA2 | 6.79 | 2.85 | 210 |
| PSA3 | 5.98 | 2.21 | 356 |
| PSA4 | 2.31 | 1.59 | 108 |

TABLE 3-continued

Adhesive performance results

| Pressure-sensitive adhesive | Bond strength to steel [N/cm] | Bond strength to PE [N/cm] | Holding power [min] |
|---|---|---|---|
| PSA5 | 2.44 | 1.03 | 168 |
| PSA6 | 2.35 | 1.22 | 155 |

For assessing the reversibility of the crosslinking, the bonded adhesives were on the one hand subjected to a climatic cycling test (variation in atmospheric humidity and in temperature) and on the other hand were treated briefly (for about 1 minute) with an acetic-acid solution. As a measure for determining the crosslinking, the elastic component was measured by the microshear test, and additionally the specimen was detached by hand from the substrate (steel).

TABLE 4

Determination of the reversibility of crosslinking via elastic component after climatic cycling test

| Pressure-sensitive adhesive | fresh | after 0.5 d 23° C. 95% rel. humidity | after 0.5 d 80° C. 95% rel. humidity | after 7 d 23° C. 95% rel. humidity | after 7 d 80° C. 95% rel. humidity |
|---|---|---|---|---|---|
| PSA1 | 7 | 6 | 7 | 5 | 7 |
| PSA2 | 25 | 23 | 20 | 24 | 22 |
| PSA3 | 52 | 50 | 51 | 54 | 53 |
| PSA4 | 74 | 73 | 73 | 71 | 72 |
| PSA5 | 77 | 72 | 69 | 68 | 65 |
| PSA6 | 80 | 79 | 77 | 80 | 78 |

It was found that the stability of the crosslinking of the adhesive activated by means of cyclic phosphonic anhydride is comparable with that of reference adhesives prepared with an ionic or a covalent crosslinker based on a polyfunctional isocyanate. For the adhesive crosslinked with Al(acac)$_3$, in contrast, a slight reduction in the elastic component is measurable, but is not sufficient for the specimen to be parted from the substrate without residue and with little application of force.

TABLE 4

Determination of the reversibility of crosslinking via elastic component after treatment with acetic acid solution

| Pressure-sensitive adhesive | fresh | after treatment | Redetachability |
|---|---|---|---|
| PSA1 | 7 | 6 | residues |
| PSA2 | 25 | 7 | no residues |
| PSA3 | 52 | 49 | poor |
| PSA4 | 74 | 73 | poor |
| PSA5 | 77 | 69 | poor |
| PSA6 | 80 | 78 | poor |

From the last series of experiments it can be seen that only the adhesive AC1 in combination with the coupling reagent could be detached easily and without residue after treatment with acetic acid solution, and that the elastic component has also dropped markedly. As soon as there is a further functionality in the polymer in addition to the carboxylic acid group, this further functionality reacting with the carboxylic acid via activation by the cyclic phosphonic anhydride, the crosslinking is irreversible and the composition is redetachable from the substrate only with difficulty and usually only with residues. The reference adhesives with the ionic crosslinker and with the isocyanate crosslinker are all difficult to detach.

It was further observed that the adhesives of the invention prepared using at least one cyclic phosphonic anhydride as crosslinking activator exhibited an optimised flame retardancy and were at least partly capable of binding calcium ions.

The invention claimed is:

1. A crosslinkable adhesive comprising
at least one polymer functionalised with organic and/or inorganic acid units containing OH groups, and at least one cyclic phosphonic anhydride.
2. The crosslinkable adhesive according to claim 1, wherein the cyclic phosphonic anhydride is a cyclic alkyl phosphonic anhydride.
3. The crosslinkable adhesive according to claim 1 wherein the cyclic phosphonic anhydride is a cyclic 2,4,6-substituted 1,3,5,2,4,6-trioxatriphosphinane 2,4,6-trioxide.
4. The crosslinkable adhesive according to claim 1 wherein the organic and/or inorganic acid units containing OH groups are carboxylic acid groups, maleic acid groups, sulphonic acid groups and/or phosphonic acid groups.
5. The crosslinkable adhesive according to claim 1 wherein the polymers functionalised with organic and/or inorganic acid units containing OH groups are further at least partly functionalised with amino groups, monosubstituted amino groups, bisubstituted amino groups, hydroxyl groups, unsubstituted phenyl radicals, substituted phenyl radicals, 1,3-diketone radicals and/or heteroaromatic compounds.
6. The crosslinkable adhesive according to claim 1 further comprising at least one polymers functionalised with amino groups, monosubstituted amino groups, bisubstituted amino groups, hydroxyl groups, unsubstituted phenyl radicals, substituted phenyl radicals, 1,3-diketone radicals and/or heteroaromatic compounds.
7. The crosslinkable adhesive according to claim 1 wherein crosslinkers are additionally present.
8. The crosslinkable adhesive according to claim 1 wherein the at least one polymer functionalised with organic and/or inorganic acid units containing OH groups comprises poly (meth)acrylate-based polymers.
9. The crosslinkable adhesive according to claim 1 wherein the adhesive is a pressure-sensitive adhesive.
10. A method for crosslinking crosslinkable adhesives comprising crosslinking an adhesive comprising at least one polymers functionalised with organic and/or inorganic acid units containing OH groups, wherein at least one cyclic phosphonic anhydride is used as crosslinking activator.
11. Method according to claim 10, wherein the cyclic phosphonic anhydride is a cyclic 2,4,6-substituted 1,3,5,2,4,6-trioxatriphosphinane 2,4,6-trioxide.
12. A pressure sensitive adhesive obtained by a method according to claim 10.

* * * * *